(12) United States Patent
Ortiz et al.

(10) Patent No.: US 9,249,171 B2
(45) Date of Patent: Feb. 2, 2016

(54) SULFILIMINE AND SULPHOXIDE METHODS FOR PRODUCING FESTINAVIR

(71) Applicant: BRISTOL-MYERS SQUIBB COMPANY, Princeton, NJ (US)

(72) Inventors: Adrian Ortiz, Hoboken, NJ (US); Tamas Benkovics, Somerset, NJ (US); Zhongping Shi, Plainsboro, NJ (US); Prashant P. Deshpande, Princeton, NJ (US); Zhiwei Guo, Sammamish, WA (US); David R. Kronenthal, Yardley, PA (US); Chris Sfouggatakis, Staten Island, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/402,231

(22) PCT Filed: May 22, 2013

(86) PCT No.: PCT/US2013/042150
§ 371 (c)(1),
(2) Date: Nov. 19, 2014

(87) PCT Pub. No.: WO2013/177243
PCT Pub. Date: Nov. 28, 2013

(65) Prior Publication Data
US 2015/0140610 A1    May 21, 2015

Related U.S. Application Data

(60) Provisional application No. 61/650,553, filed on May 23, 2012.

(51) Int. Cl.
| C07H 15/20 | (2006.01) |
| C07H 19/06 | (2006.01) |
| C12P 19/38 | (2006.01) |
| C07D 309/10 | (2006.01) |
| C07D 407/04 | (2006.01) |
| C07D 307/20 | (2006.01) |

(52) U.S. Cl.
CPC .............. *C07H 15/20* (2013.01); *C07D 307/20* (2013.01); *C07D 309/10* (2013.01); *C07D 407/04* (2013.01); *C07H 19/06* (2013.01); *C12P 19/385* (2013.01)

(58) Field of Classification Search
CPC .. C07D 307/20; C07D 309/10; C07D 407/04; C07H 15/20; C07H 19/06; C12P 19/385
USPC .......................... 544/310, 314; 549/417, 476
See application file for complete search history.

(56) References Cited

U.S. PATENT DOCUMENTS

| 7,589,078 B2 | 9/2009 | Cheng et al. |
| 8,445,669 B2 | 5/2013 | Sato et al. |
| 8,975,394 B2 | 3/2015 | Yamazaki et al. |
| 2009/0318380 A1 | 12/2009 | Sofia et al. |
| 2010/0280235 A1 | 11/2010 | Nagai et al. |
| 2012/0322995 A1 | 12/2012 | Iriyama et al. |

FOREIGN PATENT DOCUMENTS

| WO | WO 2007/038507 | 4/2007 |
| WO | WO 2009/005674 | 1/2009 |
| WO | WO 2009/119785 | 10/2009 |

OTHER PUBLICATIONS

Ortiz et al., Scalable Synthesis of the Potent HIV Inhibitor BMS-986001 by Non-Enzymatic Dynamic Kinetic Asymmetric Transformation (DYKAT), Angew. Chem. Int. Ed., vol. 54, pp. 7185-7188, 2015.*

* cited by examiner

*Primary Examiner* — Deepak Rao
(74) *Attorney, Agent, or Firm* — Dilworth IP, LLC; John F. Levis

(57) ABSTRACT

A process for making the compound of Formula I utilizes the starting compound, together with sulfilimine and sulfoxide process steps later on.

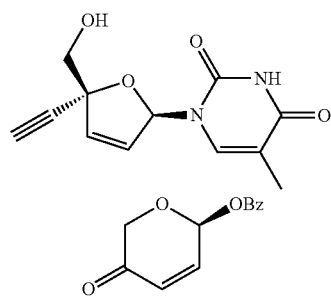

20 Claims, No Drawings

SULFILIMINE AND SULPHOXIDE METHODS FOR PRODUCING FESTINAVIR

CROSS REFERENCE TO RELATED APPLICATION

This application claims the benefit of U.S. Provisional Application Ser. No. 61/650,553 filed May 23, 2012.

FIELD OF THE INVENTION

The present invention relates to one or more methods for producing the compound festinavir. More particularly, the invention is directed to an improved method for producing festinavir in good yield utilizing a different starting material and reaction mechanism(s) than has been used to date. The invention is also directed to the intermediate compounds produced by the process(es) herein.

BACKGROUND OF THE INVENTION

The compound known as festinavir is a nucleoside reverse transcriptase inhibitor (NRTI) which is being developed for the treatment of HIV infection. The drug has shown considerable efficacy in early development, and with perhaps less toxicity than some other NRTIs, such as the drug stavudine (marketed under the trade name ZERIT®). Festinavir has the chemical formula $C_{11}N_2O_4H_8$, and the structural formula:

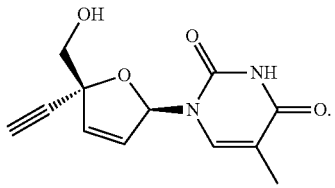 [SMILES: C#C[C@@]1(CO)C=C[C@H](n2cc(C)c(=O)[nH]c2=O)O1]

Festinavir was developed by Yale University in conjunction with two Japanese research scientists, and is protected by U.S. Pat. No. 7,589,078, the contents of which are incorporated herein by reference. The '078 patent sets forth the synthesis of the primary compound, and other structural analogs. In addition, Oncolys BioPharma, Inc. of Japan has now published US 2010/0280235 for the production of 4' ethynyl D4T. As starting raw material, the Oncolys method utilizes a substituted furan compound, furfuryl alcohol. In another publication by Nissan Chemical Industries of Japan, and set forth in WO 2011/099443, there is disclosed a method for producing a beta-dihydrofuran deriving compound or a beta-tetrahydrofuran deriving compound. In this process, a diol compound is used as the starting material. Nissan has also published WO 2011/09442 directed to a process for the preparation of a β-glycoside compound. Two further publications, each to Hamari Chemicals of Japan, WO 2009/119785 and WO 2009/125841, set forth methods for producing and purifying ethynyl thymide compounds. Pharmaset, Inc. of the U.S. has also published US 2009/0318380, WO 2009/005674 and WO 2007/038507 for the production of 4'-nucleoside analogs for treating HIV infection.

What is now needed in the art are new methods for the production of festinavir. The newly developed methods should be cost effective and obtain the final compound in relatively high yield, and should also utilize different starting material(s) and process mechanisms than what has been set forth in the published art, or is otherwise available to the skilled artisan.

SUMMARY OF THE INVENTION

In a first embodiment, the invention is directed to a process for making the compound of Formula I:

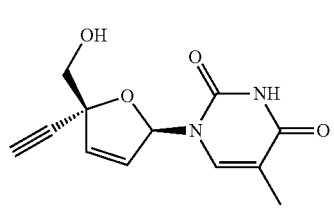

which comprises:

(1a) contacting the starting compound

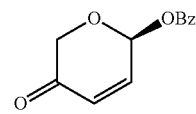

with p-thiocresol and N,N-diisopropylethylamine (DIPEA) to produce the compound 1a

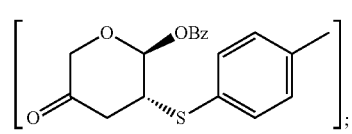

and (1b) contacting the compound 1a with the trimethylsilylation (TMS) reagent TMS-Li-acetylide in solution to yield the compound 1b

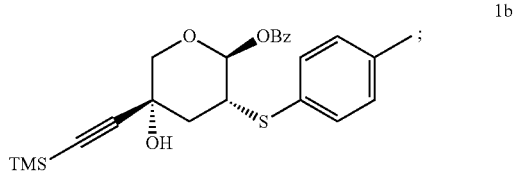

and (2) contacting the compound 1b with aqueous HCl in acetonitrile (MeCN), followed by reaction with benzoic anhydride and 4-dimethylamino pyridine (DMAP), and then reaction with aqueous $K_3PO_4$ in dimethylformamide (DMF) to yield the compound 2

3

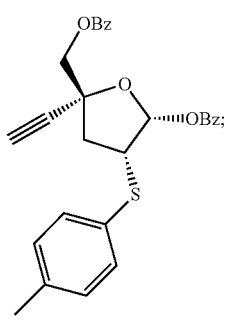

and
(3) contacting the compound 2 with the compound N,N-Bis-TMS-thymine

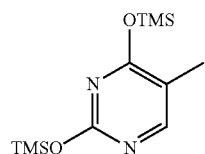

to produce the compound 3

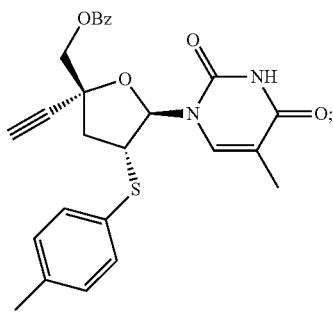

4 and (4a) contacting the compound 3 with chloramine-T or phenyliodine (bis)trifluoroacetate (PIFA) to produce the compound

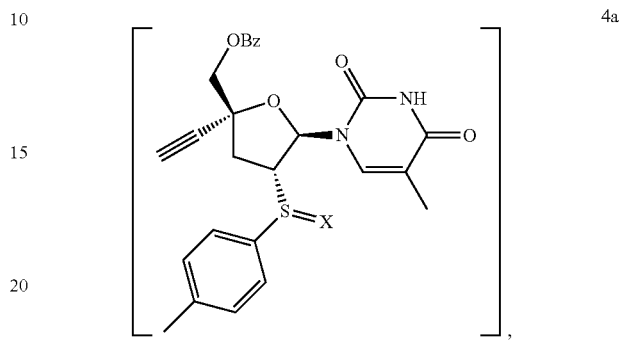

wherein X=O or NTs; and (4b) contacting the compound 4a with dimethylsulfoxide (DMSO) or n-butyl alcohol (n-BuOH), and heating to produce the compound 4b

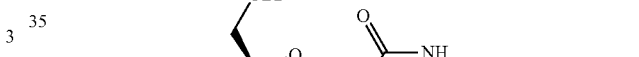

and (5) contacting the compound 4b with 1,8-diazabicycloundec-7-ene (DBU) in MeOH for benzoate removal by transesterification to yield the compound of Formula I.

Conceptually, the invention may also be summarized according to the following chemical flow diagram:

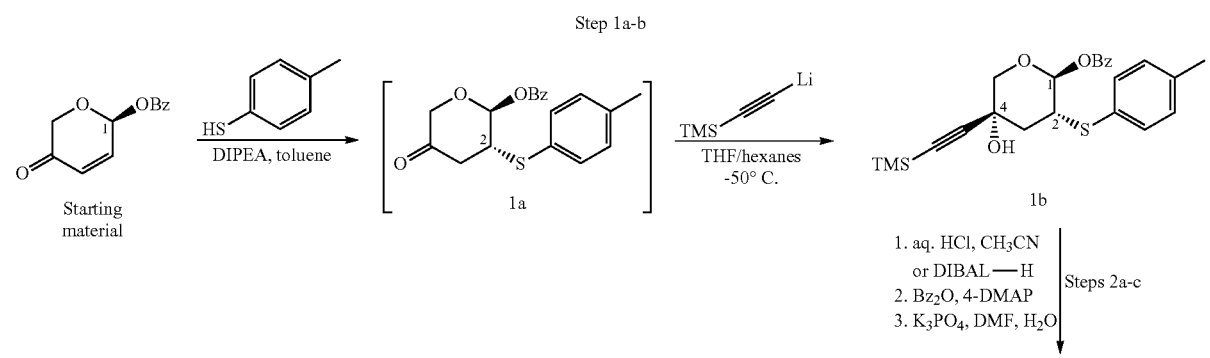

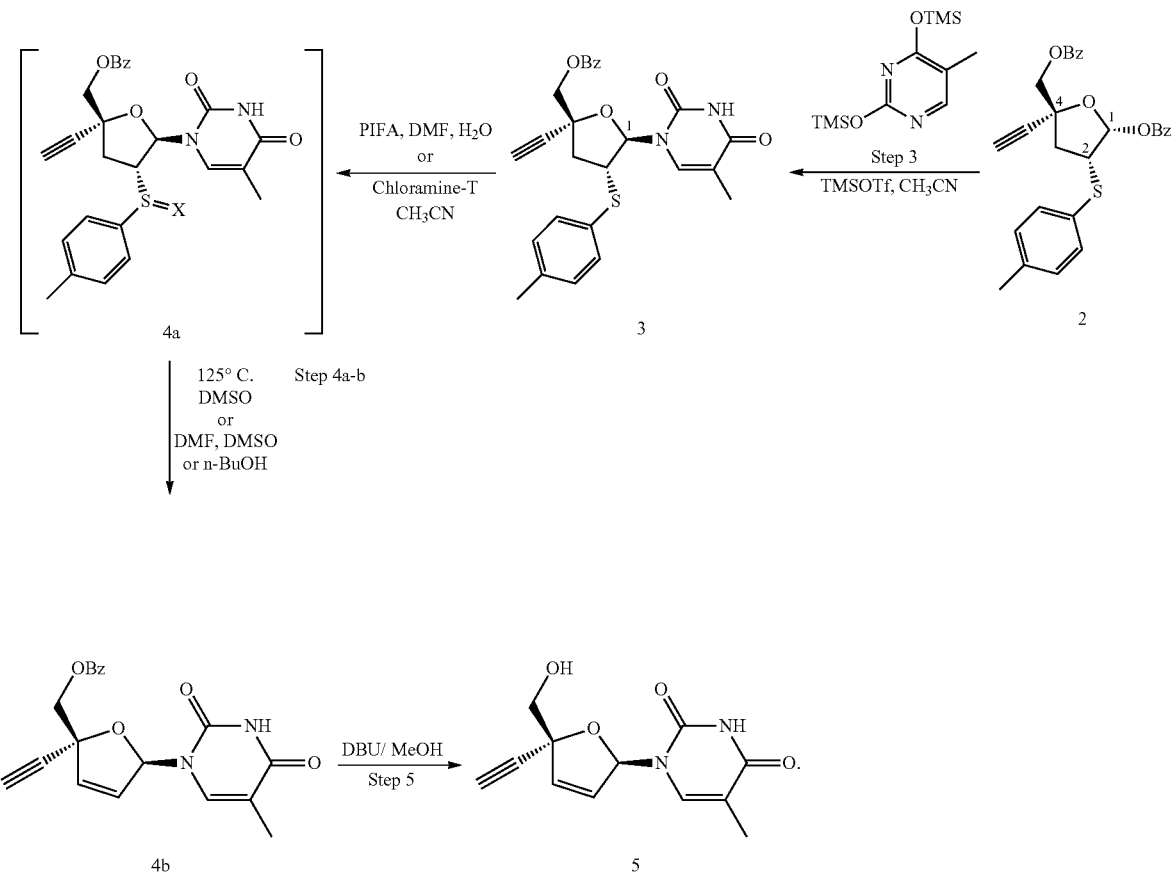

DETAILED DESCRIPTION OF THE EMBODIMENTS

In a further embodiment, the invention is also directed to one or more of each of the individual sub-steps 1a-b, 2a-c, 3, 4a-b and 5 above, whether alone or in tandem.

In another embodiment of the invention, there is also provided each of the intermediate compounds 1b, 2, 2b2, 3, 4a and 4b.

Yet other aspects and embodiments may be found in the description provided herein.

Unless otherwise specifically set forth, many chemical reagents and/or moieties have been identified herein by their commonly accepted letter abbreviations in the art for ease of reference.

Step 1a-b: Preparation of Compound 1a, then 1b

This is a two step process beginning with the base mediated conjugate addition of an aryl thiophenol, preferably p-thiocresol, to the starting compound in a toluene solution to give intermediate compound 1a. This reaction appears to be highly diastereoselective, demonstrating little or no trace of the undesired diastereomer at C-2. In a further embodiment of the invention, the —OBz group on the starting compound may be replaced with —OBR, wherein R is selected from the group of -alkyl, —OCH$_2$Aryl, -silyl, and —COR$^1$ (esters), and further wherein R$^1$ is selected from the group of -alkyl, -aryl and -cycloalkyl, with -aryl being preferred.

The second step is the reaction of TMS-Li-acetylide with the crude compound 1a solution. This is conducted by transferring the compound 1a stream to a cold (−40 to −60° C.), freshly prepared solution of TMS-Li-acetylide. When conducted at this temperature, the diastereomeric ratio, i.e. diastereoselectivity, of the alkyne addition will exceed 20:1 ratio. The product, compound 1b is isolated by crystallization from toluene/n-heptane (80% yield). In this process, two stereocenters are diastereoselectively introduced. The first (C-2) is directed by the anomeric C-1 stereocenter and the second (C-4) is controlled by of the overall conformation of the molecule as result of the C-1 and C-2 stereocenters. The reaction scheme may be summarized as follows:

Scheme 1:

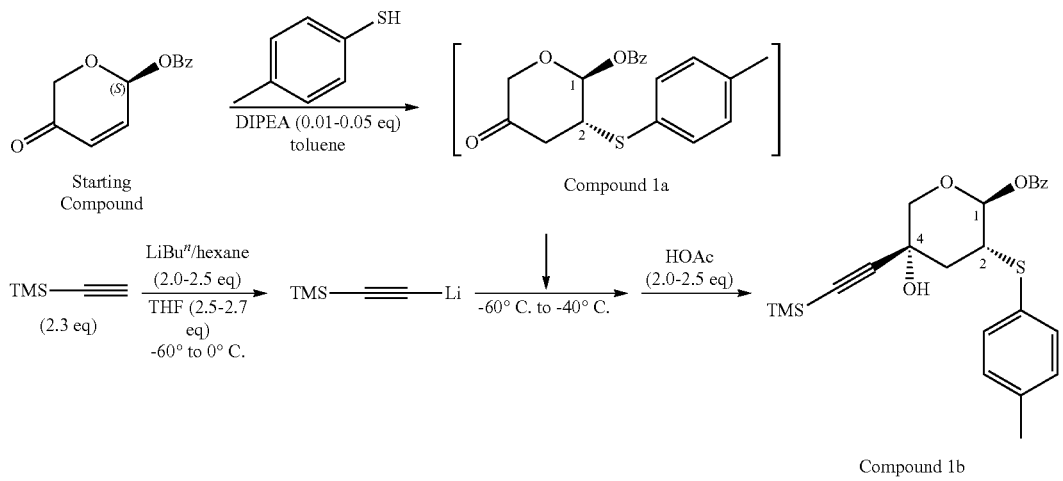

In a further embodiment of the invention, compound 1b may be represented more generically by the formula

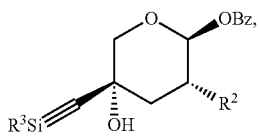

wherein $R^2$ is selected from the group of -thio-aryl, -thio-alkyl, -substituted thio-aryl, and -aryl-selenide, with -4-Me-aryl being preferred, and further wherein $R^3$ is selected from the group of -alkyl and -aryl, with -Me being preferred.

Step 2: Preparation of Compound 2

In a series of sub-steps, an important transformation of the synthetic sequence takes place as the six-membered ring monobenzoate compound 1b is converted to the five-membered ring bisbenzoate compound 2. Along the way, the TMS group is also removed from the alkyne. The steps of these synthetic operations can be effected in a number of ways, as further set forth below (see the alternative chemistry section for more details). Based on selectivity, robustness and ease of operation, it is currently preferred to utilize the sequence as outlined in Scheme 2 below.

The three-step process begins with the removal of the anomeric benzoate group present in compound 1b (step 2A). This transformation generates four lactol isomers of compound 2a: two furanose (five-membered ring) and two pyranose (six-membered ring) isomers. At least three methods have now been developed and demonstrated for this process: (1) using aqueous HCl in acetonitrile (shown below), (2) using diisobutylaluminum hydride (DIBAL-H) in toluene and (3) using an enzyme such as Lipase MY in organic/aqueous mixture. After workup, the crude lactol compound 2a is taken to the next step as a dry toluene solution.

Benzoylation of the lactol results in predominantly the desired α-furanose bisbenzoate compound 2b2 (via compound 2b1) upon treatment with about 2.5-3.5 equiv. of benzoic anhydride and about 0.1-0.5 equiv of 4-dimethylamino pyridine (DMAP, step 2B) in toluene. After reaction completion, the excess benzoic anhydride is quenched with MeOH, and the benzoic acid byproduct washed away with aqueous dibasic potassium phosphate. The toluene is then swapped to the appropriate solvent for the TMS deprotection via reduced-pressure distillation.

Selective removal of the TMS group in presence of benzyl groups can be accomplished by either treatment with $K_3PO_4$/$H_2O$ in DMF or by tetrabutyl ammonium fluoride (TBAF) in t-amyl alcohol (step 2C). Other bases which can be utilized include $K_2CO_3$, $Ce_2CO_3$, KOH, NaOH and the like. Several crystallization protocols can isolate the desired compound 2 in greater than about 60% overall yield. For instance, the material can be crystallized directly from DMF/IPA and water. Alternatively, the product can be extracted into toluene from the crude DMF solution, and compound 2 is isolated by crystallization from toluene/n-heptane.

In an alternative embodiment, $K_2PO_4$ in aqueous toluene is utilized, and a phase transfer catalyst (n-$Bu_4N^+HSO_4^-$) is employed to selectively remove the TMS group. Other $R_4N^+$ $X^-$ salts may also be employed for this embodiment. This may allow for a more efficient processing in large scale synthesis. Compound 2 can then be isolated after an aqueous work up and crystallization from toluene/heptanes.

The reaction scheme for step 2 may be summarized as follows:

Scheme 2.

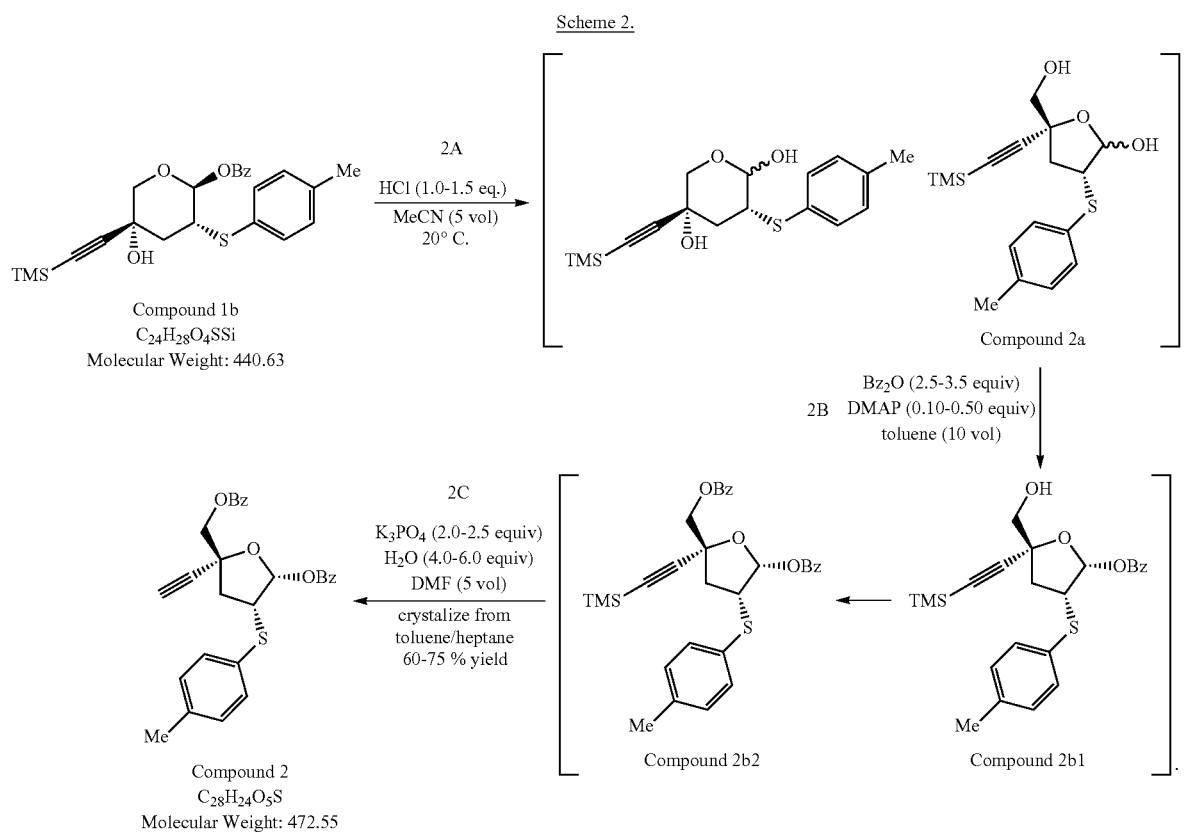

In a further embodiment of the invention, compound 2 may be represented more generically as

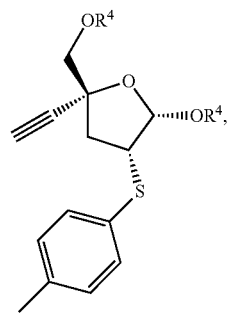

wherein $R^4$ is —$COR^5$, and $R^5$ is selected from the group of -alkyl, -aryl, and substituted aryl, with -phenyl being preferred.

In an alternative embodiment of step 2A, the HCl and MeCN are replaced with DIBAL-H in toluene. A portion of DIBAL-H reacts with the tertiary hydroxyl group in an addition controlled manner and liberates hydrogen ($H_2$ gas), and the remaining portion of DIBAL-H is necessary to remove the benzoate group. The reaction has been successfully conducted at temperatures ranging from −40 to −70° C. The reaction is initially quenched with ethyl acetate and then a reverse quench addition into aq. citric acid (20 wt %). A Rochelle's salt work up has been tested but is perhaps less desirable because of the large volumes required (150-200 vol). The toluene stream is washed with aq. $K_2HPO_4$ and then distilled to remove $H_2O$.

In a further alternative embodiment of step 2A, deprotection takes place with an enzyme such as Lipase MY in the presence of water. In organic solvent/water mixtures such as t-amyl alcohol/water or toluene/water, enzymes such as Lipase MY cleave the benzoyl group at 40° C. overnight.

In an alternative embodiment of step 2B, benzoylation first takes place using an enzyme such as Novozyme 435, for example:

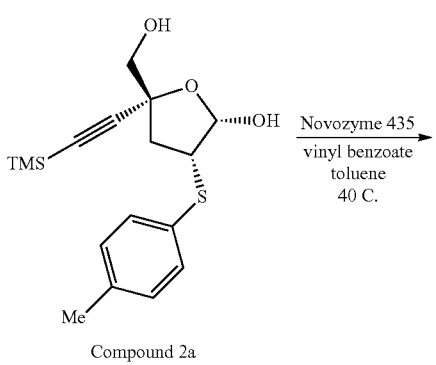

Compound 2a

-continued

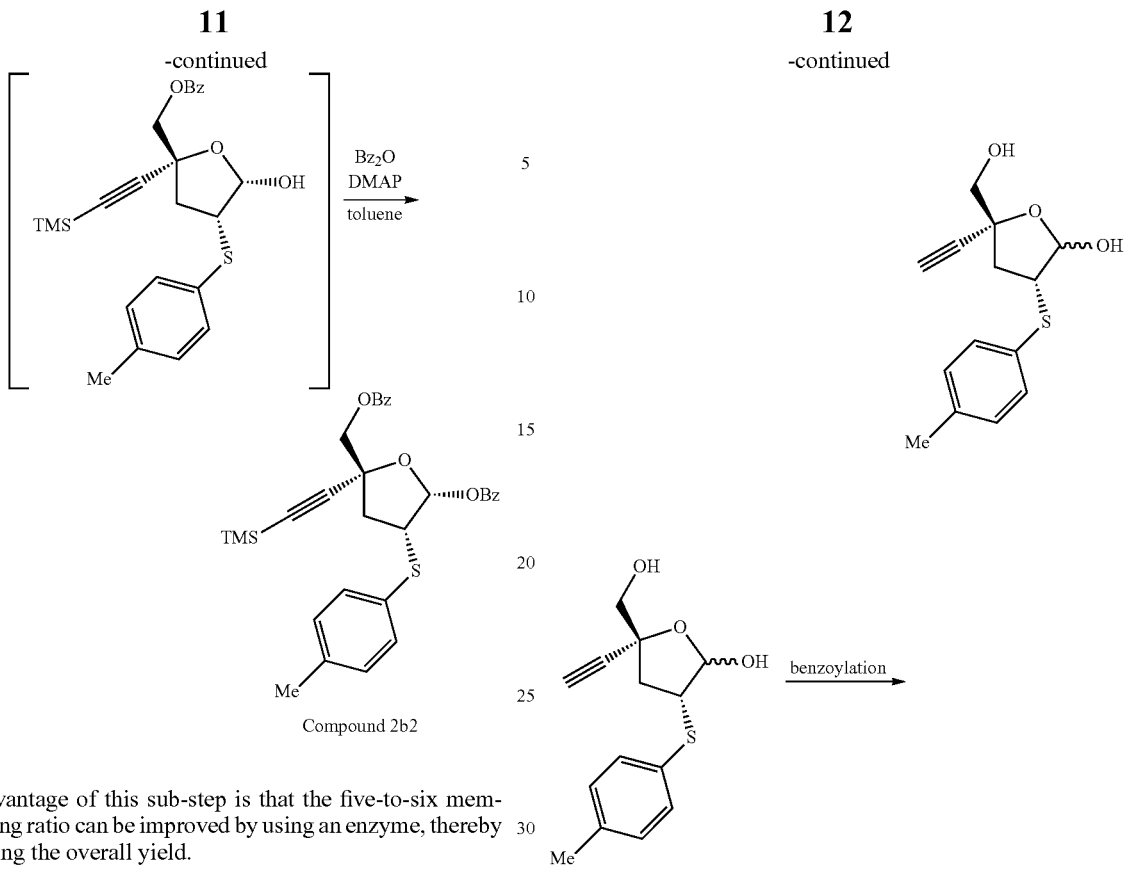

Compound 2b2

The advantage of this sub-step is that the five-to-six membered ring ratio can be improved by using an enzyme, thereby increasing the overall yield.

In an alternative embodiment of step 2C, catalytic tetrabutyl ammonium fluoride (TBAF) in the presence of water or alcoholic solvent can rapidly remove the TMS group in high yield. Other fluoride reagents such as KF, CsF, aq. HF, HF-pyridine, HF-Et₃N, DAST, NH₄F and the like may also be suitable for removal of the TMS group.

In addition, there is a further embodiment for the preparation of compound 2 wherein the TMS group is removed prior to benzoylation:

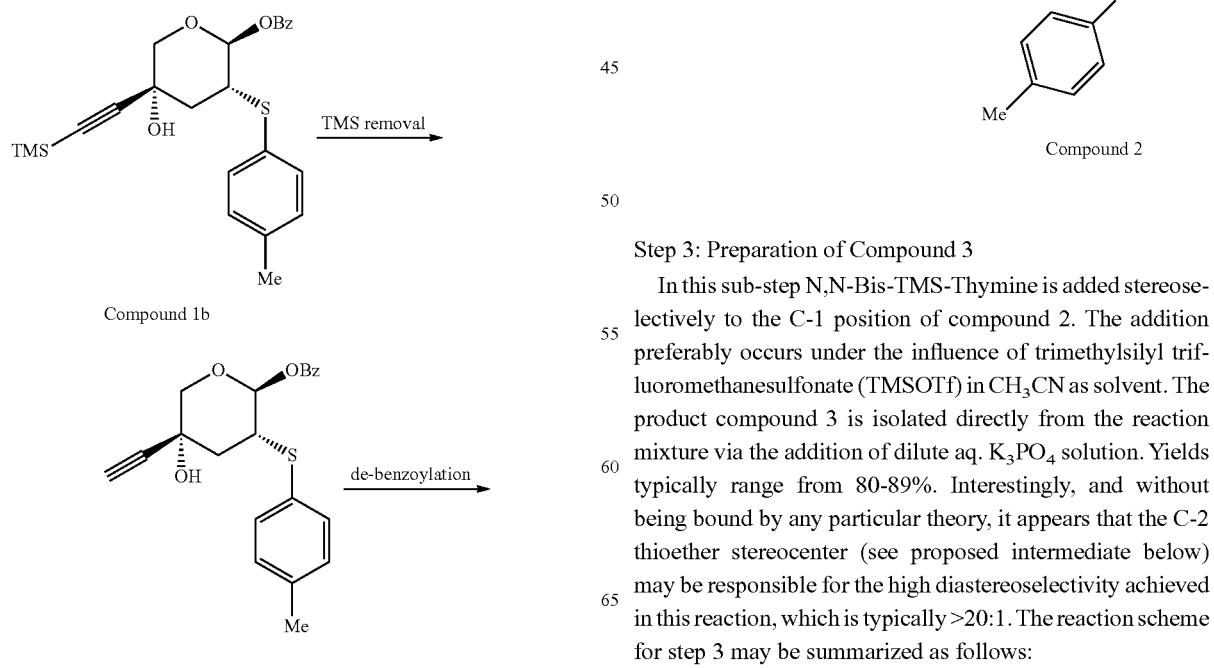

Compound 2

Step 3: Preparation of Compound 3

In this sub-step N,N-Bis-TMS-Thymine is added stereoselectively to the C-1 position of compound 2. The addition preferably occurs under the influence of trimethylsilyl trifluoromethanesulfonate (TMSOTf) in $CH_3CN$ as solvent. The product compound 3 is isolated directly from the reaction mixture via the addition of dilute aq. $K_3PO_4$ solution. Yields typically range from 80-89%. Interestingly, and without being bound by any particular theory, it appears that the C-2 thioether stereocenter (see proposed intermediate below) may be responsible for the high diastereoselectivity achieved in this reaction, which is typically >20:1. The reaction scheme for step 3 may be summarized as follows:

Scheme 3:

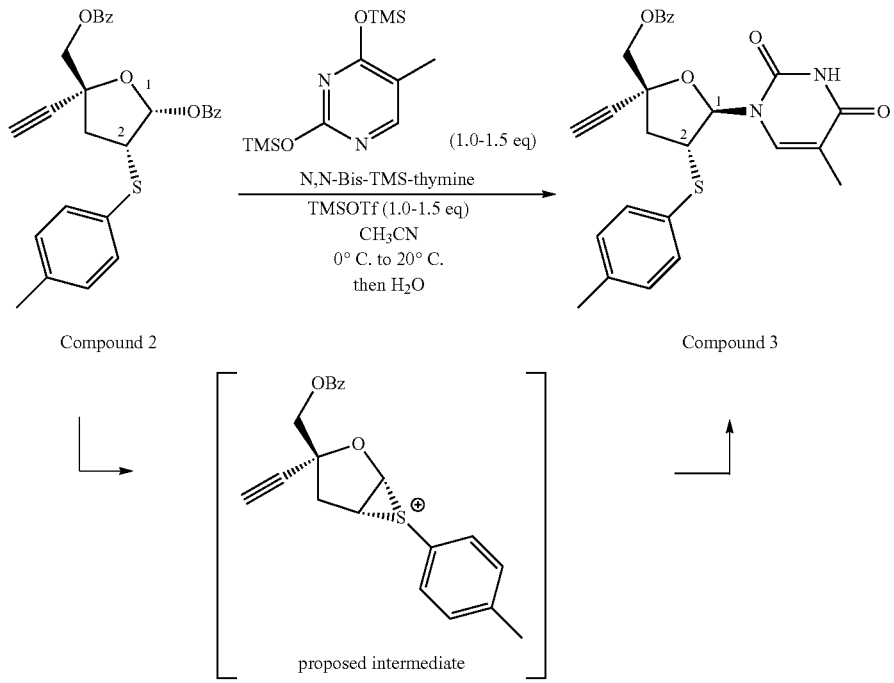

In a further embodiment of the invention, compound 3 may be represented more generically as

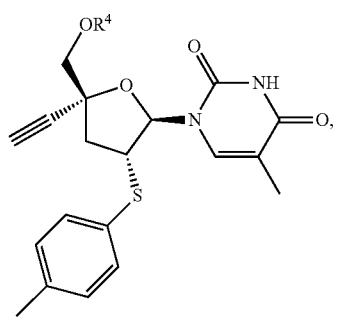

wherein $R^4$ is —$COR^5$, and $R^5$ is selected from the group of -alkyl, -aryl, and substituted aryl, with -phenyl being preferred.

Step 4: Preparation of Compound 4a, then 4b

This is a two sub-step process involving the selective oxidation of the thio ether to either a sulfilimine or a sulphoxide followed by thermal expulsion of the sulphoxide/sulfilimine to produce the requisite C-2/C-3 unsaturation. The sulfilimine method utilizes about 1.0-1.5 equivalents (eq.), preferably about 1.4 eq., of chloramine-T as stoichiometric oxidant, and is conducted in warm $CH_3CN$. At the completion of the reaction, the stream is solvent swapped to dimethyl sulfoxide (DMSO) and then heated to 125° C. for about 6-12 hours to yield Compound 4b. The sulphoxide method utilizes about 1.0-1.5 eq., preferably about 1.1 eq. of [Bis(Trifluoroacetoxy)iodo]benzene (PIFA) as the stoichiometric oxidant, and is conducted in a dimethylformamide DMF/$H_2O$ mixture. (Other reagents besides PIFA which may be utilized include, for example, $NAIO_4$, $VO(acac)_2$/t-BuOOH, m-CPBA, NBS, NCS, NIS, and $MeReO_4(MTO)/H_2O_2$.) At the end of the oxidation step, DMSO and pyridine are added and the reaction mixture is heated to 125° C. for about 6-12 hours. Typical isolated yields range from about 50-75%. The reaction scheme for step 4 may be summarized as follows:

Scheme 4:

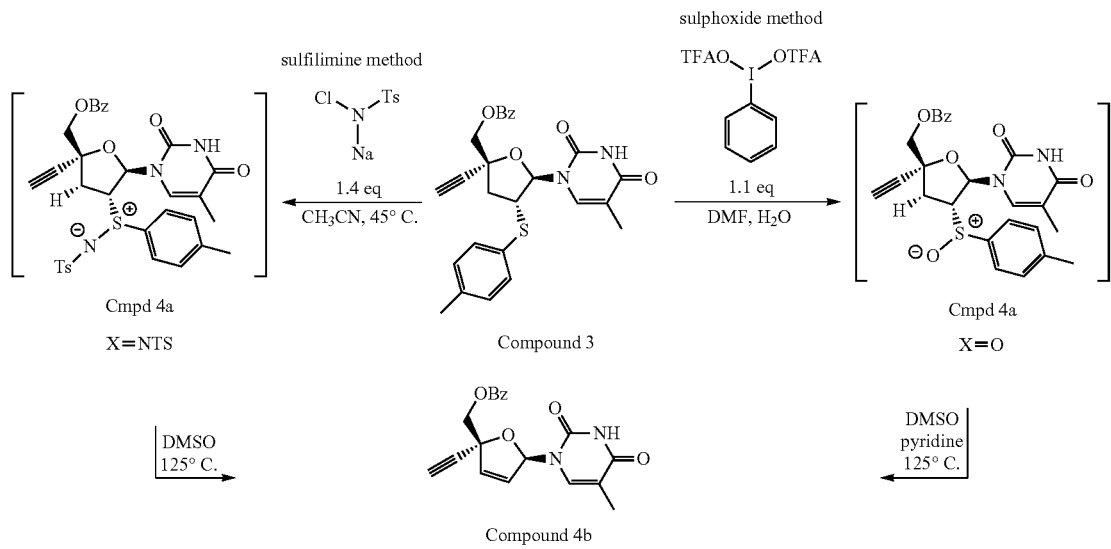

In a more preferred embodiment of the sulfilimine method set forth above, n-butyl alcohol (n-BuOH) is utilized instead of DMSO. (Other high boiling alcoholic solvents may be suitable as well, for example, n-pentanol, 4-Me-2-pentanol, isopropanol, 2-butanol, and t-amyl-OH.) This preferred method may allow for a direct drop crystallization, resulting in better quality of Compound 4b, as well as better recovery and yield. This scheme may be summarized as follows:

Step 5: Preparation of Compound 5

This is the API step comprising benzoate ester hydrolysis by NaOH in aq. tetrahydrofuran (THF) solution. The API is extracted into THF and then crystallized from THF/toluene. The reaction scheme may be summarized as follows:

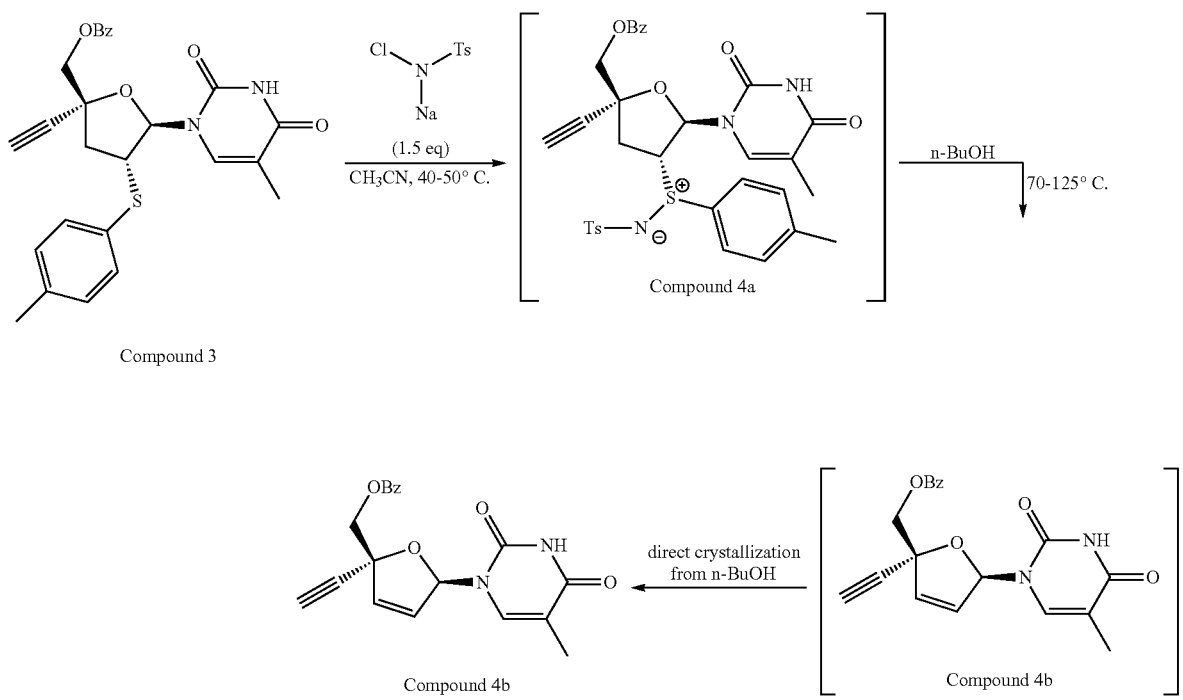

Scheme 5:

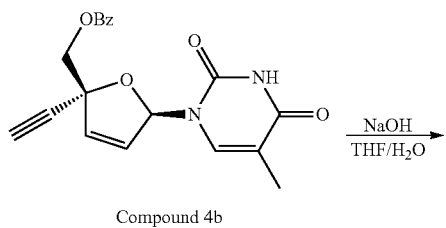

Compound 4b

Scheme 6:

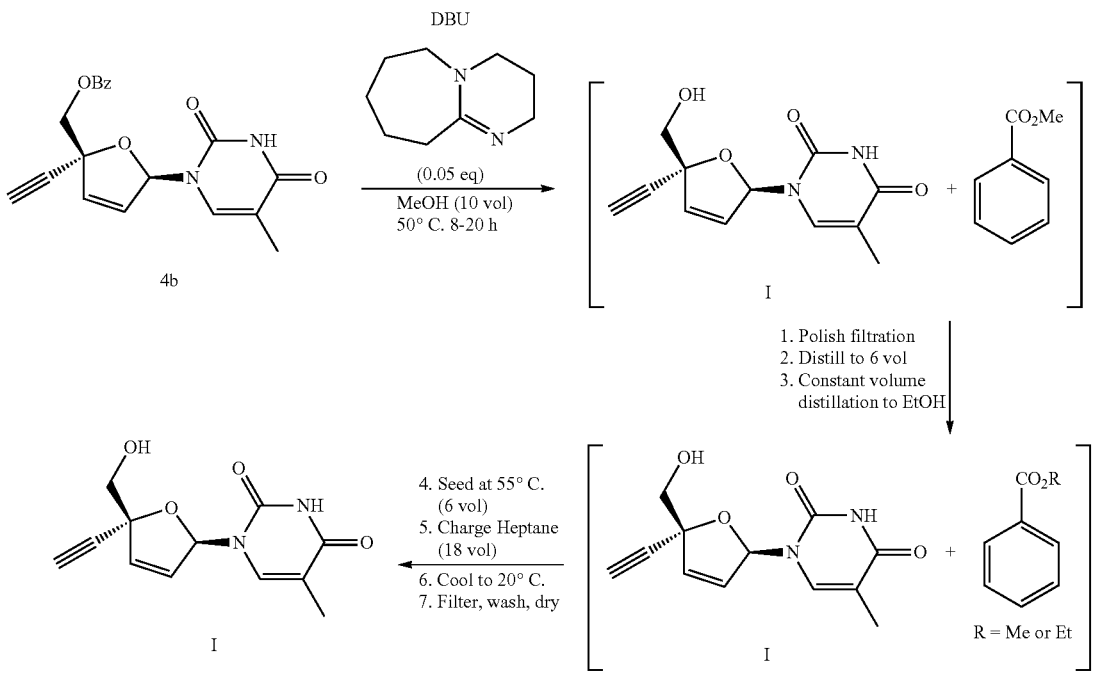

-continued

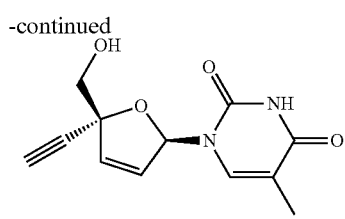

Compound of Formula I

In a further embodiment of the overall process set forth above, Step 2c described above is eliminated, thereby preserving the TMS protected derivative designated as compound 2b2, which in turn is isolated. Compound 2b2 is then reacted through steps 3 and 4, and the TMS moiety is preserved. Only during step 5, with the addition of NaOH, is the TMS moiety removed during this last step of the process.

In yet a further embodiment of this process to produce the compound of Formula I from 4b involves the 1,8-diazabicycloundec-7-ene (DBU) catalyzed transesterification of the C-5 benzoate ester protecting group to the solvent (MeOH) (see Scheme 6). This fully organic process (i.e. H$_2$O free) eliminates the need for an aqueous work up and is often more efficient than the process employing a NaOH mediated hydrolysis in aqueous THF. This process can be conducted using catalytic amounts (0.025-0.10 eq) of a variety of organic medium strength organic bases such as DBU, DBN (1,5-diazabicyclo(4.3.0)non-5-ene), or TMG (1,1,3,3,-tetramethylguanidine) with MeOH as a preferred solvent. Preferably, the reaction will proceed to completion within about 8-24 h (depending on catalyst loading). Solvent swap is performed into EtOH, and the compound of Formula I is isolated from EtOH/heptanes which provides for the desired form and particle properties of the API.

The foregoing description is merely illustrative and should not be understood to limit the scope or underlying principles of the invention in any way. Indeed, various modifications of the invention, in addition to those shown and described herein, will become apparent to those skilled in the art from the foregoing description and examples. Such modifications are also intended to fall within the scope of the appended claims.

What is claimed is:

1. A process for making the compound of Formula I

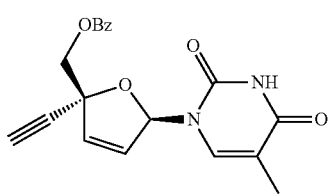

which comprises:

(1a) contacting the starting compound

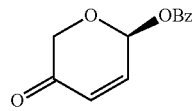

with p-thiocresol and N,N-diisopropylethylamine (DIPEA) to produce the compound 1a

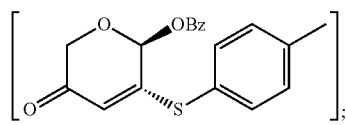

1a and (1b) contacting the compound 1a with the trimethylsilylation (TMS) reagent TMS-Li-acetylide in solution to yield the compound 1b

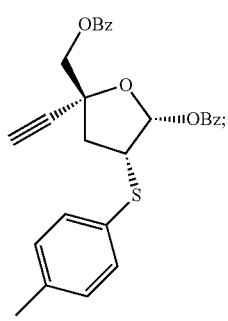

1b and (2) contacting the compound 1b with aqueous HCl in acetonitrile (MeCN), followed by reaction with benzoic anhydride and 4-dimethylamino pyridine (DMAP), and then reaction with aqueous $K_3PO_4$ in dimethylformamide (DMF) to yield the compound 2

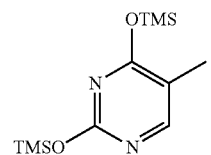

2 and (3) contacting the compound 2 with the compound N,N-Bis-TMS-thymine

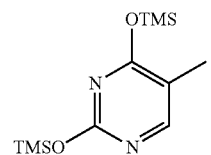

to produce the compound 3

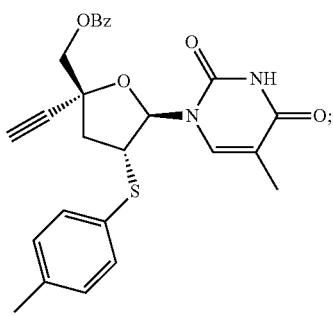

3 and (4a) contacting the compound 3 with chloramine-T or phenyliodine (bis)trifluoroacetate (PIFA) to produce the compound 4a

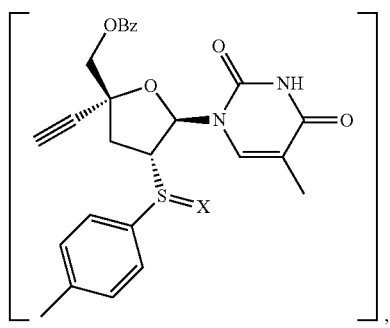

4a wherein X=O or NTs; and (4b) contacting the compound 4a with dimethylsulfoxide (DMSO) or n-butyl alcohol (n-BuOH), and heating to produce the compound 4b

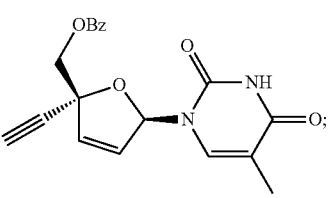

4b and (5) contacting the compound 4b with 1,8-diazabicycloundec-7-ene (DBU) and MeOH, or NaOH in THF, for benzoate ester hydrolysis to yield the compound of Formula I.

2. The process of claim 1, further comprising the crystallization of the compound of Formula I from step (5).

3. The process of claim 2, wherein said crystallization takes place using EtOH/heptanes, or tetrahydrofuran (THF) in toluene.

4. The process of claim 1, wherein said solvent in step (1a) is toluene.

5. The process of claim 1, wherein said solution in step (1b) is a cold solution of THF.

6. The process of claim 5, wherein said solution is at a temperature of about −40° C. to −60° C.

7. The process of claim 1, wherein said compound 2 is crystallized from a mixture of toluene and heptane.

8. The process of claim 1, wherein said N,N-Bis-TMS-thymine in step (3) is in a solution of trimethylsilyl trifluoromethane sulfonate (TMSOTf) in acetonitrile.

9. The process of claim 1, wherein said chloramine-T is in acetonitrile solution.

10. The process of claim 1, wherein said PIFA is in a DMF and water solution.

11. The process of claim 1, wherein in step (5) said NaOH is in aqueous THF solution.

12. The process of claim 1, wherein in step (2) said HCl in acetonitrile is replaced with diisobutylaluminum hydride (DIBAL-H) in toluene.

13. The process of claim 1, wherein in step (2) said HCl in acetonitrile is replaced with Lipase MY in organic solvent and water.

14. A process for making the compound 1b, which comprises:

(1a) contacting the starting compound

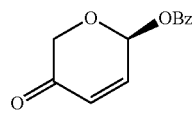

with p-thiocresol and N,N-diisopropylethylamine (DIPEA) to produce the compound 1a

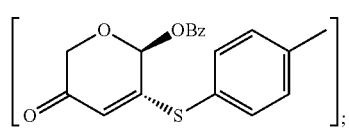

and (1b) contacting the compound 1a with the trimethylsilylation (TMS) reagent TMS-Li-acetylide in solution to yield the compound 1b

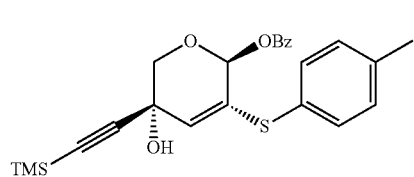

15. A process for making the compound 2, which comprises:

contacting the compound 1b with aqueous HCl in acetonitrile (MeCN), followed by reaction with benzoic anhydride and 4-dimethylamino pyridine (DMAP), and then reaction with aqueous $K_3PO_4$ in dimethylformamide (DMF) to yield the compound 2

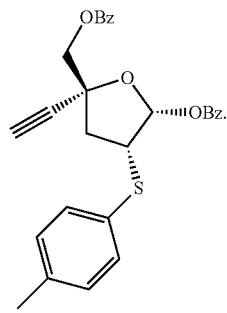

16. A process for making the compound 3, which comprises: contacting the compound 2 with the compound N,N-Bis-TMS-thymine

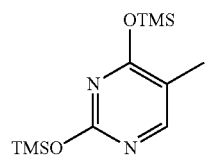

to produce the compound 3

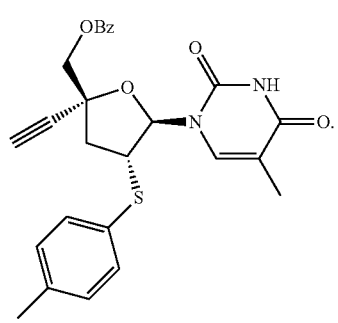

17. A process for making the compound 4b, which comprises:

contacting the compound 3

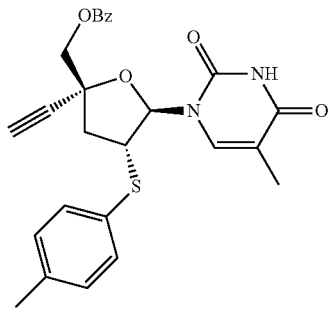
3 with chloramine-T in acetonitrile to produce the compound

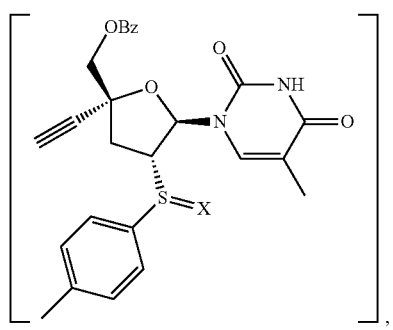
4a wherein X=NTs; and (4b) contacting the compound 4a with dimethylsulfoxide (DMSO) or n-butyl alcohol (n-BuOH), and heating to produce the compound 4b

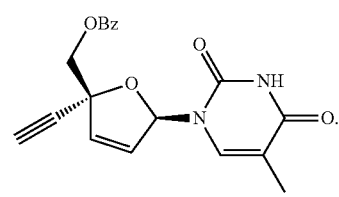
4b

18. A process for making the compound 4b, which comprises:

contacting the compound 3

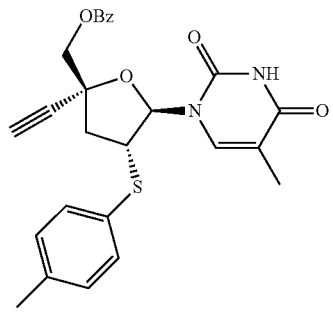
3 with PIFA in toluene/water mixture to produce the compound

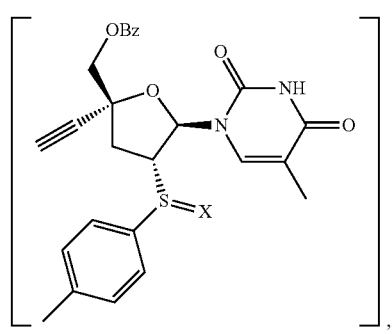
4a wherein X=O; and (4b) contacting the compound 4a with dimethylsulfoxide (DMSO) and heating to produce the compound 4b

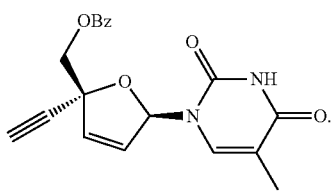
4b

19. A process for producing the compound of Formula I:

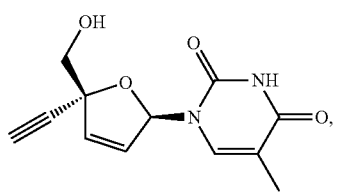
I which comprises reacting the compound 4b
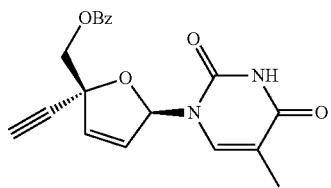
4b
with DBU in MeOH, or NaOH in THF.
20. An intermediate compound which is selected from the group consisting of the compounds 1b, 2, 2b2, 3 and 4a:
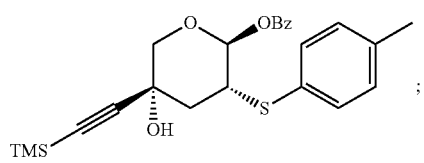
1b
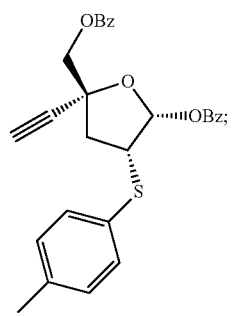
2
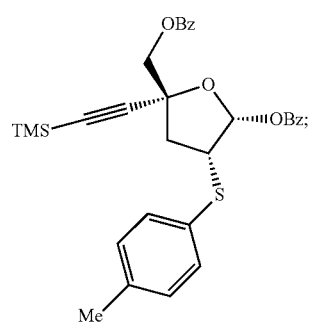
2b2
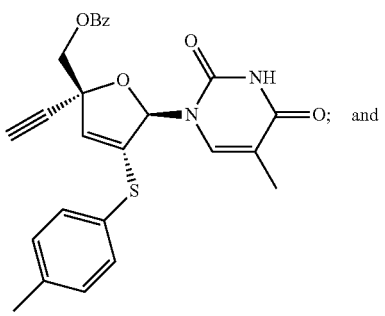
3
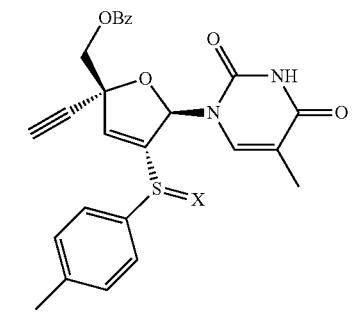
4a
wherein X is O or N-Ts.
* * * * *